US00PP24488P3

(12) United States Plant Patent
Olesen

(10) Patent No.: US PP24,488 P3
(45) Date of Patent: May 27, 2014

(54) COMPACT FLORIBUNDA ROSE PLANT NAMED 'POULPAL037'

(50) Latin Name: ***Rosa* hybrid**
Varietal Denomination: Poulpal037

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 34 days.

(21) Appl. No.: 13/507,028

(22) Filed: May 31, 2012

(65) Prior Publication Data

US 2013/0326758 P1 Dec. 5, 2013

(51) Int. Cl.
*A01H 5/00* (2006.01)

(52) U.S. Cl.
USPC ..... Plt./143

(58) Field of Classification Search
USPC ..... Plt./143, 141
See application file for complete search history.

*Primary Examiner* — Kent L Bell

(57) ABSTRACT

A new garden rose plant of the Compact Floribunda class which has abundant, pink and yellow bi-color flowers and attractive foliage. This new and distinct variety has shown to be uniform and stable in the resulting generations from asexual propagation.

1 Drawing Sheet

Botanical designation: *Rosa* hybrid.
Variety denomination: 'Poulpal037'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2003 and the resulting seeds were planted in a controlled environment in Fredensborg, Denmark. The new variety, named 'Poulpal037', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant pink and yellow bi-color flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal037' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulpal037' was selected in the spring of 2004 by the inventor as a single plant from the progeny of the aforementioned hybridization.

Asexual reproduction of 'Poulpal037' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulpal037' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal037'. Specifically illustrated in the drawing are flowers at various stages of development, flower in parts, leaves, and stems.

DETAILED DESCRIPTION OF THE VARIETY

The following is a description of 'Poulpal037', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulac008', U.S. Plant Pat. No. 15,499 are compared to 'Poulpal037' in Chart 1.

CHART 1

| | 'Poulpal037' | 'Poulac008' |
|---|---|---|
| Petal Count | 30 with 2 to 3 petaloids | 70 to 75 |
| Flower Diameter | 55 mm | 65 to 70 mm |
| General Tonality of Flower Color | Yellow-Orange Group 15C with intonations of Red-Purple Group N66A. | Yellow Group 12A |

Flower and Flower Bud

Blooming habit: Continuous.

Flower bud:

*Size*.—Upon opening, 20 mm in length from base of receptacle to end of bud. Bud diameter is 13 mm.

*Bud form*.—Ovoid.

*Bud color*.—As sepals divide petals are Yellow-Orange Group 16C and Red Group 43B and 43C.

*Sepal inner surface*.—Color: Yellow-Green Group 144A with moderate intonations of Red-Purple Group 183C. Surface: Strong pubescence and smooth.

*Sepal outer surface*.—Color: Yellow-Green Group 144A with strong intonations of Red-Purple Group 183B. Texture: Somewhat rough.

*Sepal shape*.—Apex: Cirrhose. Base: Flat at union with receptacle.

*Sepal margin*.—Margins have strong moderate foliaceous appendages on three of the five sepals.

*Sepal size*.—28 mm long by 8 mm wide.

*Receptacle*.—Texture: Smooth. Size: 5 mm in height by 7 mm wide. Color: Yellow-Green Group 144A with weak intonations of greyed-Orange Group 166B. Shape: Funnel.

*Pedicel*.—Surface: Rough with a few small prickles and many stipitate glands that are fragrant. Length: 20 to 25 mm. Diameter: 3 mm on average. Color: Yellow-Green Group 144B with pigments the color of Greyed-Red Group 180B. Strength: Strong.

*Peduncle*.—Length: 2 to 15 cm. Diameter: 3 mm. Color: Yellow-Green Group 144A with intonations of Greyed-Red Group 178B.

Flower bud development: Flower buds are borne in clusters of 5 to 9 flower buds per stem, resembling a panicle.

Flower bloom:

*Fragrance*.—Light floral.

*Duration*.—The blooms have a duration on the plant of approximately 10 to 15 days. Petals fall cleanly away from plant after flowers have fully matured.

*Size*.—Flower diameter is 55 mm when open. Flower depth is 33 mm.

*Flower shape*.—General shape is high centered, semi double, with a high pointed center which is tightly closed.

Shape of flower, side view: Upon opening the upper portion is flat. The lower portion is a flattened convex.

Petalage: Under normal conditions, flowers have 30 petals total, 2 to 3 of which are petaloids.

General tonality of flower: Open flowers are Yellow-Orange Group 15C with intonations of Red-Purple Group N66A.

Petal color:

*Upon opening, outer petals*.—Upper surface: Yellow Group 11A with marginal intonations of Red Group 54A and Red-Purple Group N57A. The base of the petal is Yellow Group 11B. Lower surface: Yellow Group 12C with intonations of Red Group 52C.

*Upon opening, inner petals*.—Upper surface: Yellow Group 9A with marginal intonations of Red Group 40C. Lower surface: Yellow Group 11A with marginal intonations of Orange-Red Group 29A.

*After opening, outer petals*.—Upper surface: The petal base is Yellow Group 9A. The middle zone is White Group 155C. The margins are Red-Purple Group N66A. Lower surface: The base and middle zones are Yellow-Orange Group 14D. The marginal zone is Red Group 51A.

*After opening, inner petals*.—Upper surface: Yellow-Orange Group 15B. Lower surface: Yellow-Orange Group 16B.

Petals:

*Petal reflex*.—Moderately reflexed.

*Margin*.—Entire and uniform. Occasional point at the center. Weak petal undulations.

*Shape*.—Generally narrow elliptic. Apex shape: Rounded. Base shape: Acute.

*Size*.—35 mm (l)×35 mm (w).

*Texture*.—Smooth.

*Thickness*.—Average.

Petaloids:

*Size*.—25 mmn (l) by 10 mm (w).

*Quantity*.—2 to 3.

*Shape*.—Asymmetric. The Base is acute, and the apex is rounded.

*Color*.—Upper surface is Yellow-Orange Group 15B. Lower surface is Yellow-Orange Group 16B.

Reproductive organs:

*Pollen*.—None observed.

*Anthers*.—Size: 2 mm in length. Color: Yellow Group 11A. Quantity: 70 on average.

*Filaments*.—Color: Yellow Group 11A. Length: 6 mm.

*Pistils*.—Length: 8 mm. Quantity: 50 on average.

*Stigmas*.—Color: Yellow-Green Group 154D.

*Styles*.—Color: Yellow-Green Group 154D.

*Location of stigmas*.—Superior in location relative to the anthers.

*Hips*.—None Observed.

Plant

Plant growth: Upright. Plants are 35 cm in height, and 35 cm wide.

Stems:

*Color*.—Juvenile growth: Yellow-Green Group 144B with light intonations of Greyed-Red Group 178B. Mature growth: Yellow-Green Group 144A.

*Length*.—On average, canes are 20 cm from the base of the plant to the flowering portion.

*Diameter*.—7 mm.

*Internodes*.—On mature canes, there is an average distance of 30 mm between nodes.

*Surface texture*.—Young wood: Rough. Older wood: Rough.

Long prickles:

*Incidence*.—8 prickles per 10 cm of stem.

*Size*.—Average length of prickles on mature stems is 9 mm.

*Shape*.—Upper portion is linear. Lower portion is concave.

*Color*.—Juvenile prickles: Greyed-Red Group 180A. Mature prickles: Greyed-Yellow Group 162A.

Plant foliage:

*Compound leaf*.—80 to 130 mm (l)×50 to 90 mm (w).

*Quantity*.—3 leaves per 10 cm of stem on average.

*Leaf bearing angle to the stem*.—60 degrees.

*Color of juvenile foliage*.—Upper side: Yellow-Green Group 144A. Lower side: Yellow-Green Group 144A with intonations of Greyed-Orange Group 176A.

*Color of mature foliage*.—Upper side: Yellow-Green Group 147A. Lower side: Yellow-Green Group 147B.

Plant leaves and leaflets:

*Stipules*.—Size: 20 mm in length. Quantity: 2 per compound leaf. Shape: Linear, slightly broad based with outward extending apices. Margins: Finely serrated. Color: Yellow-Green Group 144A.

*Petiole*.—Length: 20 mm. Diameter: 2 mm.

*Upper surface*.—Color: Yellow-Green Group 144A.

*Lower surface*.—Color: Yellow-Green Group 144B. Observations: Stipitate glands and small prickles observed.

*Rachis*.—Length: 35 to 70 mm.

*Upper surface*.—Color: Yellow-Green Group 144A.

*Lower surface*.—Color: Yellow-Green Group 144B. Observations: Stipitate glands and small prickles observed.

*Leaflet*.—Quantity: Normal number of leaflets found on leaves in middle of the stem is 5 to 7 leaflets. Margins: Serrated. Size: Terminal leaflets on normal leaves are 30 to 55 mm in length by 26 to 38 mm wide. Shape: Generally oval. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Compact Floribunda rose class named 'Poulpal037', substantially as illustrated and described herein, due to its abundant pink and yellow bi-color flowers, disease resistance, and extended period of bloom.

* * * * *

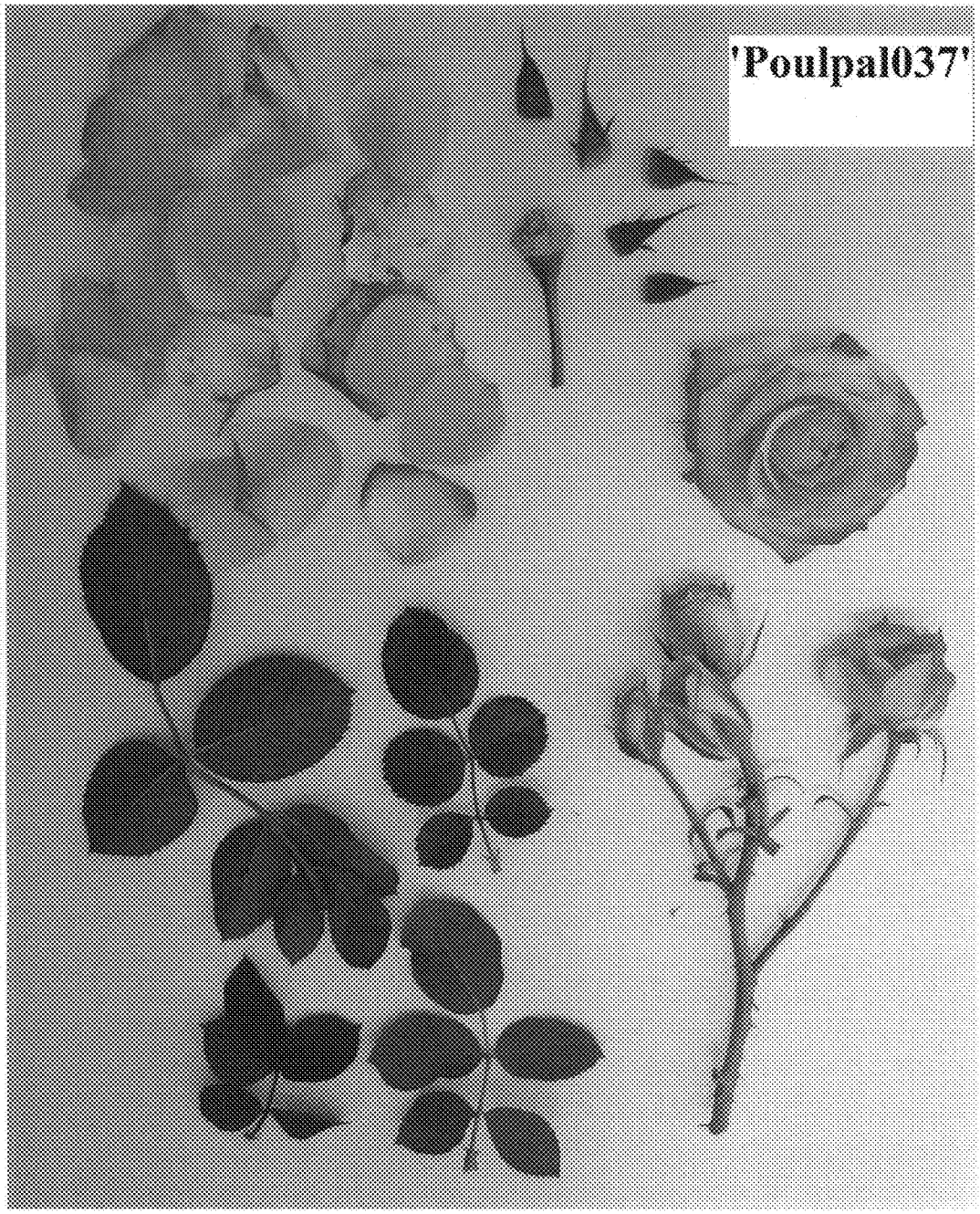
'Poulpal037'